United States Patent [19]

Rosenthaler

[11] 4,387,086

[45] Jun. 7, 1983

[54] ORGANIC COMPOUNDS

[75] Inventor: Joachim Rosenthaler, Oberwil, Switzerland

[73] Assignee: Sandoz Ltd., Basel, Switzerland

[21] Appl. No.: 184,834

[22] Filed: Sep. 8, 1980

[30] Foreign Application Priority Data

Sep. 7, 1979 [CH] Switzerland .................. 8096/79

[51] Int. Cl.$^3$ .................. G01N 33/54; G01N 33/56; G01N 33/58
[52] U.S. Cl. ........................ 436/541; 436/542; 436/543; 436/547; 436/804; 436/808; 436/815
[58] Field of Search ............... 424/1, 12; 23/230 B; 422/61

[56] References Cited

U.S. PATENT DOCUMENTS 4,197,288 4/1980 Snyder .................. 424/1

OTHER PUBLICATIONS

Chapman, Chem. Brit., 1980, 439–447.
Vanderheeren et al., Arch. Int. Pharmacodyn., 214, 86–91, 1975.
Ng et al., Br. J. Clin. Pharmac., 1977, 4, 173–183.
Rosenthaler et al., Experientia, 32/2, 234–236, 1975.
Dinovo et al., Chemical Abstracts, vol. 85, Abstract #40533n (1976).
Belpaire et al., Chemical Abstracts, vol. 84, Abstract #83975e (1976)

Primary Examiner—Christine M. Nucker
Attorney, Agent, or Firm—Gerald D. Sharkin; Robert S. Honor

[57] ABSTRACT

The invention relates to an antiserum suitable for the determination of thioridazine in blood, blood plasma and urine, the use of the antiserum and a process of determining thioridazine in blood, blood plasma or urine with the aid of this specific antiserum.

29 Claims, No Drawings

ORGANIC COMPOUNDS

The invention relates to an antiserum suitable for the determination of thioridazine in blood, blood plasma and urine, the use of the antiserum and a process of determining thioridazine in blood, blood plasma or urine with the aid of this specific antiserum.

Thioridazine is a known neuroleptic of the formula 2-methylthio-10-[2-(N-methyl-2-piperidyl)ethyl]-phenothiazine, useful for treating, inter alia, schizophrenia.

It has been found that there are large individual differences in pharmacological response to thioridazine administration. The reasons for these differences depend, for example (i) individual metabolic capacity differences, (ii) unreliability of drug intake, (iii) inter-individual absorption differences of the drug administered and (iv) drug interactions. Thus it is desirable to ascertain the optimum plasma drug level of each individual, which produces the desired neuroleptic effect and to design a dose regimen suited for the individual, e.g. a particular dosage of thioridazine, e.g. from 25 to 800 mg per day and a particular administration frequency, e.g. in divided doses 1 to 3 times a day per-orally.

The main metabolic pathways are sulfoxidation of thioridazine to the corresponding side-chain sulfoxide and sulfone. It has been observed that the number and severity of the side effects observed during a thioridazine treatment increase with the increasing level of the metabolites in the body.

Thus is is desirable to determine the amount of unchanged drug in a body fluid, such as blood, blood patients responding well to a treatment with a given plasma or urine. Comparison of such data determined in dosage of thioridazine while suffering from a minimum of side effects ("standard patient") with data found in patients not responding satisfactorily to the treatment, complaining of side effects etc. gives valuable information about the therapy to be followed.

Thus a plasma level significantly below the "standard patient" for the same dosage regimen can be due, for example, to high metabolism of thioridazine in the body or to low absorption of the drug. If it is due to the kinetics in metabolism, it may be desirable to switch to another drug. On the other hand, if the plasma level is significantly higher than that found in a "standard patient" and the patient is suffering from side effects, a decrease of the thioridazine dosage may be possible whilst still maintaining a therapeutic effect.

The amount of metabolites in the body fluid may e.g. be calculated by comparing the unchanged drug values with values obtained with unspecific methods detecting the unchanged drug together with the most important thioridazine metabolites, e.g. by means of the fluorometric evaluation method (Experientia 25, 103-104 (1969)). Another method giving information about the metabolites formed in the body is the calculation of the area under the curve wherein the amount of unchanged drug found in the blood plasma is determined in function of the time and comparison of that area with the area calculated for a "standard patient".

The various methods suitable for the determination of thioridazine in blood, blood plasma or urine e.g. the fluorometric method, liquid chromatography (HPLC) (J. Chromat. Sci. 12, 779–787 (1974)), gas chromatography (J. Pharm. Pharmacol. 21, 674–677 (1969)) and radioreceptor assay (Nature 270, 180–182 (1977)), suffer all from one or more disadvantages such as unspecificity, complexity, expensive equipment needed, etc.

Consequently, there exists a clear need for a specific method whose ease and convenience in performance meets the demands of a clinical chemistry laboratory.

We now have found that a satisfactory method for determining a suitable dose regimen is to measure the amount of unchanged thioridazine in the plasma or urine by radioimmunoassay methods. These may be surprisingly selective as to thioridazine and reject thioridazine metabolites which can also be present in the body. The method allows a very efficient drug monitoring, and it is simply and conveniently carried out by clinical laboratories using conventional equipment.

The invention therefore provides a radioimmunoassay method of specifically determining thioridazine in a body fluid sample, comprising the use of an antiserum containing antibodies specific to thioridazine and of a mixture of said body fluid and of tritiated thioridazine as antigen.

We have found, that the radioimmunoassay method is particularly selective for thioridazine when the antiserum is produced by immunogenic protein conjugates containing from particular thioridazine derivatives.

The invention provides in a further aspect an immunogenic hapten-protein conjugate capable of producing an antiserum specific to thioridazine, characterized in that the hapten is linked through a carbonyl group to a protein amine group, i.e. by an amide linkage.

Suitable haptens may be obtained by introducing, analogous to known methods, a COOH group in thioridazine. Thioridazine derivatives having a functional group selected from amino and hydroxy, e.g. in the phenyl ring are also suitable as haptens. Such thioridazine derivatives may be obtained according to known methods, e.g. by N-demethylation of 2-methylthio-10-[2-(N-methyl-2-piperidyl)ethyl]phenothiazine, and conversion of the so obtained nor derivative with an aldehyde such as formaldehyde to the corresponding N-demethyl-N-hydroxymethylthioridazine.

Conversion of thioridazine derivatives having a functional group e.g. a hydroxy group (e.g. hydroxythioridazine) with suitable halogenated carboxylic acid anhydrides yields also suitable haptens.

The following haptens are particularly suitable for use in the protein conjugate: thioridazine derivatives obtainable by conversion of a hydroxythioridazine with chloroacetic acid anhydride and particularly those obtainable by reaction of N-demethyl-thioridazine with an halogenated carboxylic acid derivative, such as chloroacetic acid anhydride or a simple dicarboxylic acid anhydride, e.g. succinic acid anhydride. N-demethylthioridazine hemisuccinate is capable of the preparation of conjugates having excellent immunogenic properties.

The conjugation of the thioridazine-derivative with the protein may then be effected analogous to coupling techniques known per se in the peptide chemistry, for example, with the aid of a coupling agent such as a carbodiimide, particularly with 1-ethyl-3-(3-dimethylaminopropyl)-carbodiimide hydrochloride.

Proteins especially suitable for the conjugation with the thioridazine haptens are e.g. serum albumin, particularly bovine serum albumin.

The hapten-protein conjugate comprises preferably 20 up to 160, more preferably 50 up to 160 thioridazine hapten residues per mol protein.

The invention further provides an antiserum suitable for the specific determining of thioridazine in blood, blood plasma or urine obtainable by immunisation of an animal with the aid of the hapten-protein conjugate of the invention. The conjugate is conveniently applied by injection, e.g. intramuscularly. Thus, the present invention also provides a process of producing the antiserum specific to thioridazine comprising administering an effective amount of the hapten-protein conjugate of the present invention to an animal, incubating the animal until a sufficient amount of antiserum has been found in the blood and isolating the antiserum.

The injection solutions or emulsions of the hapten-protein conjugates may be prepared according to methods usually applied in immunisation procedures. For example, an emulsion comprising a hapten-protein conjugate and an adjuvant having immune-stimulating properties, such as Freund's adjuvant, if desired in the presence of an adsorbent, e.g. aluminum hydroxide gel, may be used. The weight ratio of these 3 components is not critical.

The immunisation may be effected analogous to known methods by administering to a suitable animal, for example by intramuscular injection, a hapten-protein conjugate according to the invention in the form of a solution or emulsion. Suitable animals include sheep, goat, rabbit, preferably sheep, and more preferably Swiss mountain sheep. The incubation generally lasts more than 3 weeks, e.g. 5 to 10 weeks. Preferably, the incubation time is chosen to give an antiserum of a titer of above 1:2,000, e.g. of 1:7,000 to 1:10,000, the titer being defined as, the multiples of antigen at 50% binding of tracer antigen which are bound by 1 ml undiluted antiserum.

The antiserums of the invention are suitable for the determination of thioridazine in blood, blood plasma, urine, etc.

Tritiated thioridazine and processes for its preparation are known. For use in the method of the invention, it is desirable to apply tritiated thioridazine, preferably 3-[$^3$H]thioridazine, with high specific radioactivity, e.g. 36.9 mCi/mg thioridazine.

The determination of thioridazine can then be effected analogous to known radioimmunoassay methods. An advantageous method is as follows.

The lyophilized antiserum (serving as receptor protein) is dissolved and incubated together with tritiated thioridazine and unknown plasma sample. The incubation is preferably effected with cooling, preferably at 4° C. The pH of the incubation mixture is preferably kept between 5 and pH 7, e.g. pH 6, for example with the aid of a buffer, e.g. a citrate buffer.

The incubation time should conveniently last 2 hours or more, e.g. 6 to 12 hours. After incubation the free fraction is separated from the bound fraction. The separation can e.g. be effected with the aid of charcoal, e.g. dextran coated charcoal. The free fraction adsorbs onto the charcoal and may then be separated by centrifugation or filtration. The radioactivity of the whole supernatant is then measured with standard methods, e.g. liquid scintillation counting after addition of a scintillator fluid. With the aid of a standard curve it can then be easily determined what concentration corresponds to the measured radioactivity.

The selectivity of the method can be determined as follows.

The main metabolites of thioridazine having a structure closely related to the parent compound are thioridazine-derivatives oxidized in the 2-methylthio side chain, more specifically the sulfoxide (A) and the sulfone (B), and also demethyl-thioridazine (C). The cross-reactivity of the antiserum was examined by employing a mixture of thioridazine, its sulfoxide A and sulfone B and its demethyl-thioridazine C in the amount required to inhibit the reaction between antibody (antiserum) and tracer antigen (tritiated thioridazine) by 50%. No significant interference from the metabolites was observed. The inhibitory concentrations of A, B and C where 50% binding to the antiserum of Example 4 occurs, are respectively 67, 93 and 111 times higher than that of the parent compound.

The invention further provides a kit comprising tritiated thioridazine, thioridazine standard, antiserum of the invention and optionally a buffer and/or charcoal.

The tritiated thioridazine is preferably in the form of 3-[$^3$H]thioridazine hydrochloride.

One ampoule contains e.g. a solution of 60 ng tritiated thioridazine in 70% ethanol. The thioridazine standard is also preferably used in the form of thioridazine-hydrochloride, e.g. as a solution of 1.318 ng thioridazine-hydrochloride in 1 ml 70% ethanol. The antiserum is preferably supplied in lyophilized powder form. The buffer is preferably 1 M citrate of pH 5.5. The charcoal is preferably supplied in the form of an aqueous suspension e.g. 0.5 g charcoal in 2 ml twice distilled water.

The following examples illustrate the invention. Temperatures are given in centigrade.

EXAMPLE 1:

Hemisuccinate of 2-methylthio-10-[2-(2-piperidyl)ethyl]phenothiazine 110 mg (1.1 mM) Succinic anhydride are added to a solution of 357 mg (mM) 2-methylthio-10-[2(2-piperidyl)ethyl]phenothiazine in 40 ml benzene. The mixture was boiled at 90° under reflux for 90 min. and then concentrated to about 2 ml in vacuo. The dissolved crude product was purified by preparative thin layer chromatography (solvent mixture: methylene chloride/ethanol/formic acid in a ratio of 80:15:5). A Linomat III was employed to charge the silica gel plates (200×200×0.5 mm) with the product. The zone where the material was located was scraped off and the silica gel extracted by washing it with methanol. The title compound was obtained after filtration and evaporation of the solvent.

EXAMPLE 2:

Hapten-protein conjugates

Two single samples (100 mg) of hemisuccinate of 2-methylthio-10-[2-(2-piperidyl)ethyl]phenothiazine were dissolved in 5 ml 40% aqueous pyridine, and 5 ml aqueous solution of bovine serum albumin (100 mg) added thereto. An aqueous solution (1 ml) of 1-ethyl-3(3-dimethylaminopropyl)carbodiimide hydrochloride (150 mg) was added dropwise with stirring. One sample was kept for 5½ hours and the other one for 24 hours at room temperature. Unreacted low molecular weight material was removed by dialysis first against 40% aqueous pyridine, then against 10% aqueous pyridine, and finally against diluted aqueous ammonia of pH 8. The amount of hapten bound to protein was determined by UV-absorption at 314 nm. An estimated 158 hapten residues were found to be bound per mol of protein.

EXAMPLE 3:

Immunization

An emulsion consisting of 10 mg conjugate obtained according to Example 2, aluminum hydroxide gel, and Freund's compl. adjuvant in a ratio 1:1:3 was used as inoculum for immunization. Swiss mountain sheep was immunized in four divided doses by intramuscular injection in the scapular and gluteal regions. After three weeks the sheep was given a booster injection of the same composition. A five week incubation time was needed to obtain an antiserum with a titre of approx. 1:10,000.

EXAMPLE 4:

Methodology

4.1 The following kit was used.

(a) Antiserum

Lyophilized antiserum from sheep is supplied as powder in 10 ml ampoules. For preparation of the batch the antiserum was diluted in a 1:76 ratio with 0.15 M phosphate buffer of pH 6 containing 1% dextran (Serva No. 18680) and 0.2% sodium azide (Merck No. 6688). A titer of 1:7,600 was determined. The powder is dissolved, before use by adding 10 ml twice distilled water.

(b) $^3$H-Tracer

3-[$^3$H]Thioridazine-hydrochloride of a specific radioactivity of 36.9 mCi/ng was used. The content of one ampoule (60 ng $\hat{=}$ 2.21 $\mu$Ci) which is dissolved in 1 ml 70% ethanol should be diluted with buffer (9.0 ml) up to 10.0 ml.

(c) Standard 1.318 ng Thioridazine-hydrochloride is dissolved in 1 ml 70% ethanol under nitrogen gas. This amount is equivalent to 1.200 ng free base.

Identification of the compound:

UV-absorption spectrum: Range 200-400 nm, c' (g/l)=0.2786 (in methanol)

| Maxima at | $\lambda$(nm) | log $\epsilon$ |
|---|---|---|
| | 262 | 4.586 |
| | 314 | 3.659 |

| Elemental analysis (RTH 1046) | | | | |
|---|---|---|---|---|
| | C | H | N | Cl | S |
| Calc. | 62.0 | 6.7 | 6.9 | 8.7 | 15.8 |
| Found | 61.8 | 6.9 | 6.8 | 8.7 | 15.8 |

Melting point observed 161°-163°.

Preparation of the dilution series:

An aliquot of the above solution, e.g. 0.1 ml diluted with 0.9 ml plasma ($\hat{=}$12 ng/0.1 ml) serves as stock solution. Donor plasma or predose plasma is equally suitable, but it should not contain phenothiazine or interfering substances. From this, further dilutions are made by using always plasma, e.g. by diluting 0.5 ml stock solution with 0.5 ml plasma, and so on to obtain the dilution series 6, 3, 1.5, 0.75, 0.38 and 0.19 ng/0.1 ml.

(d) Buffer concentrate

The concentrate which is supplied with the Kit is 1 M citrate of pH 5.5. For the preparation of the concentrate, 588 g (tri-) sodium citrate dihydrate (Merck No. 6448) and 48 g citric acid monohydrate (Merck No. 244) were dissolved in 2 liters twice distilled water. 10 g sodium azide was added, and the pH was controlled. One ampoule contains 10 ml concentrate. Before use, this must be diluted with twice distilled water up to 200 ml. The pH of this final solution is 6.0 $\pm$0.1.

(e) Preparation of coated charcoal

One ampoule contains a suspension of 0.5 g charcoal (Merck No. 2186) in 2 ml twice distilled water. Before use, this suspension is diluted with 50 ml buffer. Coating is achieved by adding to this 1 ml donor or predose plasma. The final suspension must be cooled to 4°.

4.2 Methodology

The following Table 1 is followed when pipetting the amount (ml) of the various reagents into the tubes (in the order given below from left to right): TA (total radioactivity), NSB (non specific binding=radioactivity not adsorbed by charcoal in the absence of antibody), Bo (bound labelled ligand at zero dose of unlabelled ligand), ST (standards), UNK (unknowns). To the samples which do not contain plasma (TA, NSB, Bo) 0.1 ml donor or predose plasma must be added.

TABLE 1

| | Buffer | Plasma | Standard | Tracer | Antiserum | Charcoal |
|---|---|---|---|---|---|---|
| TA | 1.5 | 0.1 | — | 0.1 | — | — |
| NSB | 1.0 | 0.1 | — | 0.1 | — | 0.5 |
| Bo | 0.9 | 0.1 | — | 0.1 | 0.1 | 0.5 |
| ST | 0.9 | — | 0.1 | 0.1 | 0.1 | 0.5 |
| UNK | 0.9 | (0.10)(*) | — | 0.1 | 0.1 | 0.5 |

(*)volume of unknown plasma sample necessary after an oral dose of 25 mg thioridazine-HCl in man.

As shown in the above scheme, 0.1 ml plasma sample is necessary to assay the unknown after an oral dose of 25 mg thioridazine in man. If, because of a higher dose less plasma should be required the volume may be reduced to 50 $\mu$l and this is then diluted with an equal volume donor or zero dose plasma.

After pipetting buffer, plasma or unknown, respectively and standard and tracer into the tubes, the content is stirred on a whirly mixer, and then antiserum added. Immediately thereafter, the tubes are shaken again and then incubated between 2-6 hours at 4°. After the incubation, 0.5 ml ice-cooled coated charcoal suspension is added to all tubes except TA. After that, they are incubated for 10 minutes at 4°. As usual, this step depends mostly on proper timing.

The thioridazine to be measured competes with the labelled species for the available binding sites on the antibody. Separation of bound from unbound labelled ligand is accomplished by adsorption of the free compound on charcoal. The radioactivity of the soluble ligand receptor complex is then measured by liquid scintillation counting.

To keep the procedure reproducible, the tubes are centrifuged batch-wise for 5 minutes at 1,200 xg in a refrigerated centrifuge at 4°. The whole supernatant is decanted into vials containing 10 ml Rialuma ® (a scintillator liquid of LUMAC). This is mixed thoroughly by shaking them all together and the radioactivity of the samples is measured either for 10 minutes, or until 10K is counted.

In any case, cpm which are measured by liquid scintillation counting must be corrected for quench, and the absolute values should be recorded as disintegrations per minute.

A commercially available programme should be employed to calculate the unknown concentrations from the dose/response relationship.

Since more than 10 ml of a certain scintillation solution may be needed to dissolve 1.7 ml supernatant one is required to choose those proportions between them which yield a thoroughly clear solution for scintillation counting.

EXAMPLE 5:

Clinical trial

In a clinical trial where 14 geriatric patients participated plasma and urine samples have been analysed fluorometrically.

The plasma samples and some urine specimens were also analysed by radioimmunoassay. The patients received one single 25-mg coated thioridazine tablet Melleril® (Sandoz). They were of either sex and were aged from 68 to 91 years with a body weight of 46 to 74 kg. Subjects with severely impaired hepatic or renal function, or some malabsorption syndrome have been excluded. No restrictions of the food and drink intake have been placed but, concurrent medication was kept to a minimum during the study. No other phenothiazines have been allowed. Before commencing the investigation blood and urine samples from the patients have been examined by several routine clinical control tests. Tables 2 and 3 give the timing of blood and urine samples and the results obtained by either method. Obviously, the mean plasma concentrations found by fluorimetry are about 3 to 8 times higher than those analysed by radioimmunoassay. The ratio of the concentrations measured fluorometrically to those measured by radioimmunoassay ($C_{FLU}/C_{RIA}$) is lowest soon after drug intake and grows bigger to a maximum after 24 hours. This is parallel to the increasing amount of metabolites which, at least partially is measured by fluorimetry. On the other hand the time for mean peak plasma concentration ($\bar{x}$) is the same when determined by either method. The long time for $c_{p,max}$ found in this study can possibly be attributed to the patients' confinement to bed where gastrointestinal motility most probably is reduced. Likewise it could be also a result of the decline in the integrity of the systems involved in intestinal absorption.

Integration of the plasma-level versus time curve between the limits time zero and infinite time yields an area under the curve which is about 7 times smaller when assaying the plasma samples by radioimmunoassay as against fluorimetry.

Similar inferences apply to the renally excreted amount. The mean percentage of the dose excreted with the urine amounts to 4.6±1.9% as measured fluorimetrically. About 0.2% of the dose is detected in urine as parent drug when the samples are analysed by radioimmunoassay.

In conclusion, it appears that this radioimmunoassay is highly specific for parent drug, that it has a detection limit (1.8 ng/ml) which is low enough to measure plasma levels after a single 25-mg dose, that test performance is accurate and that it may fill a gap on the palette of available tests for thioridazine.

TABLE 2

PLASMA LEVELS AFTER A SINGLE ORAL DOSE OF ONE TABLET (25 MG) MELLERIL® TO GERIATRIC PATIENTS MEASURED FLUORIMETRICALLY ($C_{FLU}$ IN NG THIORIDAZINE-BASE/ML)

| PATIENT | TIME (H) | | | | | | | | | |
|---|---|---|---|---|---|---|---|---|---|---|
| | 0.5 | 1 | 2 | 4 | 8 | 12 | 24 | 48 | 72 | 96 |
| 1 | 278 | 802 | 757 | 737 | 716 | 707 | 527 | 275 | 114 | 57 |
| 2 | 0 | 13 | 191 | 414 | 681 | 710 | 602 | 487 | 355 | 260 |
| 3 | 0 | 0 | 0 | 181 | 545 | 490 | 315 | 197 | 104 | 60 |
| 4 | (7) | 89 | 670 | 813 | — | — | 423 | 299 | 95 | 57 |
| 5 | (3) | 30 | 466 | 669 | 645 | 639 | 439 | 81 | 113 | 57 |
| 6 | 0 | 12 | 79 | 250 | 385 | 302 | 156 | 73 | 31 | 15 |
| 7 | (8) | 74 | 215 | 281 | 306 | 295 | 287 | 182 | 88 | 44 |
| 8 | 0 | 0 | 134 | 214 | 235 | 238 | 315 | 327 | 296 | 235 |
| 9 | 0 | 18 | 214 | 265 | 226 | 178 | 84 | 21 | 12 | (3) |
| 10 | 0 | 0 | (9) | 45 | 490 | 574 | 559 | 526 | 430 | 331 |
| 11 | 0 | 0 | 61 | 349 | 458 | 490 | 355 | 138 | 61 | 32 |
| 12 | 0 | 0 | 0 | 56 | 297 | 318 | 124 | 32 | (6) | 0 |
| 13 | 0 | 0 | 0 | 544 | 548 | 484 | 360 | 178 | 74 | 27 |
| 14 | 0 | 15 | 289 | 327 | 283 | 262 | 144 | 66 | 27 | 12 |
| $\bar{x}$ | 22 | 75 | 220 | 367 | 447 | 437 | 335 | 201 | 129 | 85 |

(—) no sample available
( ) below detection limit (= 10 ng/ml)

TABLE 3

PLASMA LEVELS AFTER A SINGLE ORAL DOSE OF ONE TABLET (25 MG) MELLERIL® TO GERIATRIC PATIENTS MEASURED BY RADIOIMMUNOASSAY ($C_{RIA}$ IN NG THIORIDAZINE-BASE/ML)

| PATIENT | TIME (H) | | | | | | | | | |
|---|---|---|---|---|---|---|---|---|---|---|
| | 0.5 | 1 | 2 | 4 | 8 | 12 | 24 | 48 | 72 | 96 |
| 1 | 93.0 | 130.0 | 99.7 | 77.3 | 61.8 | 55.0 | 37.5 | 19.0 | 9.1 | 5.9 |
| 2 | 0 | 5.9 | 61.4 | 86.6 | 97.2 | 89.3 | 59.1 | 45.0 | 27.0 | 20.4 |
| 3 | 0 | 0 | 3.8 | 37.9 | 66.3 | 51.8 | 27.7 | 14.2 | 9.4 | 5.4 |
| 4 | 0 | 41.8 | 101.4 | 86.5 | — | — | 15.7 | 8.5 | 5.1 | 2.9 |
| 5 | 0 | 9.8 | 72.2 | 79.4 | 56.6 | 49.0 | 29.2 | 12.1 | 7.9 | 4.7 |
| 6 | 0 | 4.5 | 22.6 | 40.7 | 38.1 | 28.3 | 15.3 | 7.1 | 4.4 | 0 |
| 7 | 7.5 | 43.7 | 88.6 | 68.6 | 60.6 | 51.0 | 32.1 | 21.2 | 7.0 | 3.0 |
| 8 | 0 | 6.3 | 99.3 | 136.9 | 129.4 | 136.2 | 135.2 | 101.9 | 103.8 | 79.3 |
| 9 | 0 | 7.1 | 83.7 | 55.1 | 39.0 | 23.1 | 11.0 | 4.2 | 2.9 | 0 |
| 10 | 0 | 0 | 0 | 35.3 | 194.7 | 148.8 | 108.4 | 72.9 | 50.6 | 37.7 |
| 11 | 0 | 0 | 29.7 | 95.7 | 85.2 | 80.8 | 34.1 | 10.6 | 5.5 | 2.0 |
| 12 | 0 | 0 | 0 | 14.9 | 61.5 | 42.0 | 16.7 | 7.2 | 2.7 | 2.0 |

TABLE 3-continued

PLASMA LEVELS AFTER A SINGLE ORAL DOSE OF ONE TABLET (25 MG) MELLERIL® TO GERIATRIC PATIENTS MEASURED BY RADIOIMMUNOASSAY ($C_{RIA}$ IN NG THIORIDAZINE-BASE/ML)

| PATIENT | TIME (H) | | | | | | | | | |
|---|---|---|---|---|---|---|---|---|---|---|
| | 0.5 | 1 | 2 | 4 | 8 | 12 | 24 | 48 | 72 | 96 |
| 13 | 0 | 0 | 0 | 96.9 | 67.4 | 50.2 | 30.9 | 13.8 | 6.0 | 3.4 |
| 14 | 0 | 9.8 | 81.5 | 69.1 | 46.7 | 41.8 | 21.8 | 10.9 | 5.4 | 3.0 |
| $\overline{X}$ | 7.2 | 18.5 | 53.1 | 70.1 | 77.3 | 65.2 | 41.1 | 24.9 | 17.6 | 12.1 |
| +/−S.D. | 24.8 | 35.2 | 41.5 | 31.5 | 43.1 | 38.8 | 36.6 | 28.8 | 27.9 | 21.8 |
| $\dfrac{C_{FLU}}{C_{RIA}}$ | 3 | 4 | 4 | 5 | 5.8 | 6.7 | 8.2 | 8.1 | 7.3 | 7.0 |

$\overline{X}$ = mean plasma level
+/−S.D. = standard deviation

I claim:

1. A radioimmunoassay method for specifically determining thioidazine in a body fluid, comprising the steps of
   (1) conjugating a thioridazine derivative with a protein to obtain a hapten-protein conjugate of thioridazine,
   (2) administering said hapten-protein conjugate into an animal capable of developing antiserum to said conjugate,
   (3) incubating said conjugate in said animal for a sufficient time to permit development of said antiserum,
   (4) collecting said antiserum,
   (5) tritiating thioridazine,
   (6) incubating the antiserum, tritiated thioridazine and unknown plasma sample so as to permit binding in accordance with standard radioimmunoassay techniques, and
   (7) measuring the radioactivity of the bound thioridazine and comparing it to a standard curve to ascertain thioridazine concentration.

2. The method of claim 1 wherein the thioridazine derivative contains a carbonyl, an amino or an hydroxy moiety.

3. The method of claim 2 wherein the protein is a serum albumin.

4. The method of claim 2 wherein the thioridazine derivative is N-demethyl-N-hydroxymethylthioridazine or hydroxythioridazine.

5. The method of claim 2 wherein the antiserum is incubated together with radiolabelled thioridazine and said body fluid containing thioridazine.

6. The method of claim 5 wherein the incubation is effected at 4° C. for at least two hours.

7. The method of claim 6, in which the pH during incubation is kept between pH 5 and pH 7.

8. The method of claim 7, in which the pH is pH 7.

9. The method of claim 8, in which the pH is controlled with the aid of a buffer.

10. The method of claim 9, in which the buffer is a citrate buffer.

11. The method of claim 1, in which the thioridazine fraction not bound to the antiserum is separated by adsorption to charcoal and consequent centrifugation or filtration.

12. The method of claim 11, in which the charcoal is dextran coated charcoal.

13. As a mercantile unit, a kit suitable for use in specifically determining thioridazine in a body fluid, comprising at least one container of tritiated thioridazine, thioridazine standard, and antiserum prepared by
   (1) conjugating a thioridazine derivative with a protein to obtain a hapten-protein conjugate of thioridazine,
   (2) administering said hapten-protein conjugate into an animal capable of developing antiserum to said conjugate,
   (3) incubating said conjugate in said animal for a sufficient time to permit development of said antiserum, and
   (4) collecting said antiserum.

14. The kit of claim 13, comprising a buffer and/or charcoal.

15. An immunogenic hapten-protein conjugate capable of producing an antiserum specific to thioridazine comprising a thioridazine derivative containing a carbonyl, amino or hydroxy group and linked through said group to a protein suitable for imparting such immunogenicity to the conjugate.

16. The conjugate of claim 15, in which the hapten is N-demethyl-thioridazine condensed with an anhydride of a dicarboxylic acid.

17. The conjugate of claim 15, in which the hapten is N-demethyl-thioridazine-N-hemisuccinate.

18. The conjugate of claim 15, in which the protein is a serum albumin.

19. The conjugate of claim 18, in which the protein is bovine serum albumin.

20. The conjugate of claim 15, comprising 20 to 160 hapten residues per mole protein.

21. The conjugate of claim 15, comprising 50 to 160 hapten residues per mol protein.

22. An antiserum suitable for the specific determination of thioridazine, obtainable by immunisation of an animal with the aid of the hapten-protein conjugate of claim 15.

23. The antiserum of claim 22, in which the animal is a goat or a rabbit.

24. The antiserum of claim 22, in which the animal is a sheep.

25. The antiserum of claim 22, in which the animal is a Swiss mountain sheep.

26. A process of producing the antiserum specific to thioridazine comprising administering an effective amount of a conjugate of claim 15 to an animal, and incubating the animal until a sufficient amount of antiserum has been formed in the blood, and isolating antiserum.

27. N-Demethylthioridazine-N-hemisuccinate.

28. N-Demethylthioridazine-N-hemisuccinate-hydrochloride.

* * * * *